United States Patent
Rashwan (10) Patent No.: US 10,463,679 B2
(45) Date of Patent: Nov. 5, 2019

(54) COMPRESSED CAPSULES FOR GIVING BIRTH TO MALES

(71) Applicant: Emad Abd Elazeem Rashwan, Somoha Alexandria (EG)

(72) Inventor: Emad Abd Elazeem Rashwan, Somoha Alexandria (EG)

( * ) Notice: Subject to any disclaimer, the term of this patent is extended or adjusted under 35 U.S.C. 154(b) by 0 days.

(21) Appl. No.: 16/310,641

(22) PCT Filed: Jun. 27, 2016

(86) PCT No.: PCT/EG2016/000020
§ 371 (c)(1),
(2) Date: Dec. 17, 2018

(87) PCT Pub. No.: WO2018/001440
PCT Pub. Date: Jan. 4, 2018

(65) Prior Publication Data
US 2019/0183906 A1    Jun. 20, 2019

(51) Int. Cl.
| | | |
|---|---|---|
| *A61K 31/57* | (2006.01) | |
| *A61K 31/196* | (2006.01) | |
| *A61K 31/573* | (2006.01) | |
| *A61K 31/7016* | (2006.01) | |
| *A61K 33/14* | (2006.01) | |
| *A61K 9/48* | (2006.01) | |
| *A61K 9/50* | (2006.01) | |

(52) U.S. Cl.
CPC ............ *A61K 31/57* (2013.01); *A61K 9/4858* (2013.01); *A61K 9/5057* (2013.01); *A61K 31/196* (2013.01); *A61K 31/573* (2013.01); *A61K 31/7016* (2013.01); *A61K 33/14* (2013.01)

(58) Field of Classification Search
CPC .... A61K 31/57; A61K 9/4858; A61K 9/5057; A61K 31/196; A61K 31/573; A61K 31/7016; A61K 33/14
See application file for complete search history.

(56) References Cited

U.S. PATENT DOCUMENTS

2003/0224065 A1    12/2003 Sweazy et al.

OTHER PUBLICATIONS

International Search Report for International Application No. PCT/EG2016/000020 dated Mar. 23, 2017.
Jean-Francois Husson et al., Traitements par ka fludrocortisone, Jan. 24, 2003, pp. 41-53, http://www.cnhim.org/dossier du cnhim-pdf/dossiers/articles/dossier 2003, 1 fludrocortisone.pdf.

*Primary Examiner* — Sahar Javanmard
(74) *Attorney, Agent, or Firm* — Clements Bernard Walker (57) ABSTRACT

The present invention is related to baby love male capsules including active ingredients such as fludrocortisone, bumetanide, sodium bicarbonates, sodium chloride, and Licourice extract, inactive ingredients such as gelatin, plasticizers, moisture absorbents, and preservatives.
The active ingredients are selected according to ovum wall thickness and cell fragility theories. The present invention leads to a breakthrough in the medical field through which the baby gender can be determined and many chronic diseases can be cured.

1 Claim, 2 Drawing Sheets

COMPRESSED CAPSULES FOR GIVING BIRTH TO MALES

FIELD OF THE INVENTION

The present invention is related to a novel medical composition for helping in giving birth to males. The present invention is based on two theories in modern medicine, which have been capable of answering many confusing questions, such as:

Can we choose the sex of the baby? Why do some women give birth only to females? Why do other women give birth only to males? Why do some couples have unexplained infertility in spite of having no health-related issues?

BACKGROUND OF THE INVENTION

The first steps of theory finding took place in 1970, when Landrum Shettles and David Rorvik, two of the most famous obstetricians and gynecologists in USA, published their famous book "How to choose the sex of your baby?"

They explained that the male (Y) sperm is smaller, lighter and faster than the female sperm (X). They proposed a new theory on how to give birth to boys and girls. The theory is based on the ovulation timing. They recommended that parents desiring a girl are encouraged to have sex three or four days before ovulation. The weaker and smaller male sperm will die within the first two days while the stronger and bigger female sperm will be able to live longer and fertilize the ovum once released from the ovary. On the other hand, it is better for boy-desiring couples to have sex closest to the time when a woman's ovum is released, giving better chance for the male sperm to fertilize the ovum.

Upon starting to put the theory into practice, researchers were divided into two groups. One group supports the theory, claiming 75% success rate as mentioned in the article published by the Independent (UK) in 2002 under the title "Can you choose your baby's sex?" by Roger Dobson and republished on 25 Aug. 2006 by Independent Online. The other group strongly opposes the theory, on the grounds that scientific evidence and data tend to disprove it, as claimed in an article entitled "Gender Selection Methods by Intercourse Timing: Review of Published Scientific Articles" (fertilityfriend.com) 1998-2006.

The above-mentioned article listed the following three researches as refuting Shettles theory:
(John T. France and colleagues, for example, in an article published in 1992 in The International Journal of Fertility say " . . . our findings tend to disprove the Shettles theory . . . " Likewise, R H Gray, in a 1991 article in American Journal of Obstetrics and Gynecology says that the Shettles method is contradicted by scientific data. Finally, in a 1995 study published in the New England Journal of Medicine, researchers Allen Wilcox, Clarice Weinberg and Donna Baird say that "the timing of sexual intercourse in relation to ovulation has no bearing on the sex of the baby.")

However, prior researches suffer some disadvantages. I believe that Shettles theory includes the following mistakes:
1. The theory could not explain the logical but not factual assumption that "if the male sperm always reaches the ovum first, then all the babies must be boys."
2. Shettles claimed that boy-desiring couples must have intercourse just before ovulation. This is definitely wrong since the bigger and stronger female sperm will then have a better chance to reach the ovum and fertilize it before the male sperm.
3. Shettles did not know that there are factors, of course after Allah's Will, that determine the sex of the baby other than the intercourse timing. I believe that the thickness of the ovum wall is the most important factor representing the major obstacle encountering sperms. Hence, baby love male capsules attenuate the coat of the ovum, so that the male sperm can reach the ovum first.

The theory of the ovum wall thickness explains the most important factor determining the sex of the baby. On the other hand, the theory of cell fragility offers an ideal solution for treating the thickness of the ovum wall. It also offers a solution for some types of infertility and chronic diseases for which modern medicine cannot offer a cure.

BRIEF SUMMARY OF THE INVENTION

The present invention provides a novel and easy-to-use drug, designed in the form of capsules or tablets which are easy to swallow. The novel drug satisfies the needs of many couples, whether the newly-wed ones desiring to have a boy as their first child or those having female children and desiring to have boys or vice versa. Accordingly, it may help each family to enjoy a desired social and psychological balance.

The drug, according to the present invention, also provides a solution and treatment for couples suffering from unexplained infertility and for women having polycystic ovary syndrome or undergoing recurrent miscarriage.

The drug, according to the present invention, may also help those suffering from chronic diseases for which medicine provided no cure, such as knee osteoarthritis, rheumatoid, lupus erythematosus, psoriasis, autoimmune diseases, AIDS, and Hepatitis B & C.

The theory of cell fragility provides a treatment not only for a thick ovum wall but also for all the body cells, including immune cells. Having an increased salt intake and blood alkalosis and eating much ginger tend to reduce the excess activity of the immune system, thus giving rise to autoimmune diseases. On the other hand, one can increase immunity by reducing one's salt intake, increasing blood acidity by eating orange, lemon, Seville orange and vinegar, depending on natural sources of sugar (such as honey, fruits and pumpkin) and consuming some herbs (such as black cumin, Echinacea, and ginseng)—and having cupping done (on the anatomical surface of the liver and immune areas). By increasing immunity, diseases such as AIDS and Hepatitis B & C can be cured. This general theory of cell fragility may also be used in other medical specialties, such as orthopedics, ophthalmology, neurology, oncology, etc.

The idea of the novel drug is based on two modern theories:

The first theory is named "ovum wall thickness". It assumes that the outer coat of the ovum differs in thickness from one woman to another depending on the number of layers comprised in the corona radiata encapsulating the ovum coat. References state that an ovum wall consists of three components:
  Ovum plasma membrane
  Zona pellucida
  Corona radiata encapsulating zona pellucida The main factor undergoing increase and decrease is the layers of the corona radiata. References state that it consists of one to six layers or even more. They encapsulate the coat of the ovum. Hence, if the number of layers of corona radiata becomes smaller (1-2), then the ovum coat is thin. On the other hand, if the number of layers becomes larger (5 or more), then the ovum coat is thick. An average coat thickness reaches 3-4 layers of corona radiata.

Shettles and Landrum found that the male sperm, which is smaller, lighter and faster, always reaches the ovum first. This finding was later confirmed by researches, such as the Microsoft method, which is used for choosing the gender of the baby in ICSI. If the ovum wall is thin, then the male sperm will be able to burrow the coat of the ovum and the baby will thus be a boy. If the ovum wall is thick, the weak male sperm will not be able to burrow the coat, which will then be burrowed by the stronger female sperm and the baby will thus be a girl. In case the ovum wall is of an average thickness, then both the male and female sperms will have a chance to fertilize the ovum, as will be illustrated below in the detailed description.

The above-mentioned theory explains why some women give birth only to females while others give birth only to males or even to both sexes. It also explains some types of unexplained infertility where the couples have no health-related issues but no pregnancy occurs. Estimates show that about 7% of couples have unexplained infertility. In these cases, the wife has a thick ovum wall (5 layers or more) and the sperm count of the husband is in the lowest normal range. However, sperms cannot burrow the thick wall of the ovum. Accordingly, no fertilization occurs and the case is diagnosed as infertility because of the thickness of the ovum wall.

The second theory is named "cell fragility". It offers a solution and treatment for the complications of a thick/thin ovum wall. If the ovum is thick, the woman gives birth only to females and if the ovum is thin, she gives birth only to males. The theory also offers a solution for a number of chronic diseases for which there is no cure.

The theory depends on the scientific fact that water is responsible for perfusing the cells. If no enough water reaches the living cells, they suffer dehydration, causing cell fragility and weakness. If enough water reaches the living cells, they become stronger. This is the mechanism of action of the novel drug, according to the present invention.

BRIEF DESCRIPTION OF THE DRAWINGS

The present invention is illustrated and described herein with reference to the drawing, in which like reference numbers denote like method steps and/or system components, respectively, and in which.

DETAILED DESCRIPTION OF THE INVENTION

The two theories will be explained in further detail below. The detailed description illustrates the composition according to the present invention and the preparation method thereof, which is based on the two theories, with reference to the accompanying figures (FIGS. 1-11).

I obtained the following five pieces of information from scientific references, online medical sites, and practical life.
1. The male sperm is smaller, lighter and faster than the female sperm.

More than forty years ago, Landrum B. Shettles and David M. Rorvik, two of the most famous obstetricians and gynecologists in USA in their famous book "How to choose the sex of your baby?" explained that the male sperm is smaller, lighter and faster than the female sperm.

The Shettles method, first formally theorized in the 1960s by Landrum B. Shettles, proposes that sperms containing the X (female) chromosome are more resilient than sperms containing the Y (male) chromosome (France and Graham, et al. 1984). The method advocates intercourse two to four days prior to ovulation. By the time ovulation occurs, the cervix should contain a higher concentration of female sperms still capable of fertilization (with most of the male sperms already dead). Intercourse close to ovulation, on the other hand, should increase the chances of conceiving a boy since the concentration of the Y sperm is to be higher at the height of the menstrual cycle (Gray, 1991).

Later researches confirmed this piece of information. One of these researches is an article published by the Independent (UK) in 2002 by Roger Dobson under the title "Can You Choose Your Baby's Sex? The female chromosome is substantially larger than the male chromosome. As a result, sperm cells having an X chromosome will contain approximately 2.8 percent more DNA than sperm cells having a Y chromosome. The Microsort method for sex selection is based on this fact and is used in IVF centers. A dye is added to the sperm and the sperm with a bigger head is chosen to be implanted inside the ovum for couples desiring a baby girl. Sperm with a smaller head is implanted inside the ovum for those desiring a baby boy. Success rates are reported to be 88% for those X-bearing sperm, and 73% for the Y-bearing sperm. The British writer says that this method drove several British people to travel to USA to go through Microsoft.

2. Conception during summer gives a better chance for having a baby boy.

In its issue 2360, NewScientist magazine published an article by Kate Douglas on 14 Sep. 2003 under the title "Boy or girl?" The writer said in the article, "More boys are born after unseasonably hot weather."

3. Salty foods help in having a baby boy.

The site of the French Assembly for Sex Selection said that salty foods and red meat are ideal for those trying to have a boy (without presenting an explanation for this). The same information was given on the medical site www.Baby2see.com under the title "Improving chances of conceiving a boy or a girl."

4. Acidity and alkalinity of the female genital system help in conceiving boys and girls. Many medical sites, such as the site of the French Assembly for Sex Selection, info@choosethegenderofyourbaby.com, and pregnancy&childbirth.com, said that controlling the acidity and alkalinity is one of the factors for choosing the baby's sex.

5. One man may have different wives who give birth to different sexes (boys and girls), while a woman may be married many times while giving birth to only one sex each time (a piece of information derived from practical life).

I considered the above-mentioned five pieces of information along with the following Hadiths and Qur'anic verses.

The Prophet (peace be upon him) said, "If (during intercourse) a man's ejaculatory fluid precedes the woman's, then the child will be a boy, and if the woman's precedes the man's then the child will be a girl," and "If man's fluid comes on top, then the child will resemble the father, and if the woman's fluid comes on top, then the child will resemble the mother."

Allah says in Surat Ash-Shura, "To Allah belongs the Kingdom of the heavens and the earth. He creates whatever He decides; He bestows upon whomever He decides females, and He bestows upon whomever he decides the males. Or He couples them, (both) male and female and He makes whomever He decides sterile. Surely He is Ever-Knowing, Ever-Determiner." (Verses 49-50)

I tried to interpret the above-mentioned Hadiths and verses in light of the five pieces of information. Considering the first Hadith, I found that there is some sort of a real race between the X-bearing sperm and the Y-bearing sperm. If the X-bearing sperm precedes the Y chromosome and fertilizes the egg, then the child will be a boy if Allah so wills and vice versa. Man's semen is a fluid having two chromosomes, the X-bearing chromosome (female sperm) and the Y-bearing chromosome (male sperm). If man's fluid (male sperm Y) precedes the woman's fluid (female sperm X) and fertilizes the ovum, then the child will be a boy. If the woman's fluid (female sperm X) precedes the man's fluid (male sperm Y) and fertilizes the ovum, then the child will be a girl.

This interpretation of the Hadith is supported by the following two verses in the Qur'an in which Allah says, "And that He created the two pairs, the male and the female. From a sperm drop when it is ejaculated." (Surat An-Najm, verses 45-46).

This means that Allah (Glorified be He) created males and females from a Nutfah (sperm drop), which refers to man's fluid. The author of "At-Tahrir wat-Tanwir" says that a sperm drop is very tiny and the meaning of "ejaculated" is to utter suddenly and vehemently. It is known that man's fluid is ejaculated vehemently and that is why it is called semen. Semen includes the sperm drop from which boys and girls are created.

Definitely, Allah (Glorified be He) and His Messenger (peace be upon him) address people in a way understandable to them so that they will not disbelieve the Revelation. The Prophet (peace be upon him) used to address the people using concise yet most comprehensive expressions so that all the people might understand what he says.

By considering the above-mentioned verses of Surat Ash-Shura, I found that couples are divided into four groups:
1. A group giving birth only to females
2. A group giving birth only to males
3. A group giving birth to both males and females
4. A group not giving birth at all A man may either be fertile (having no sperm-related problems) or infertile (having sperm-related problems). Likewise, a woman may be fertile or infertile. Infertile men and women stand for the fourth group, who are incapable of giving birth. On the other hand, fertile men and women stand for the first three groups. A normal man has 50% male sperms and 50% female sperms. The male sperm always precedes the female one (as confirmed by the first piece of information). Accordingly, the baby must always be a boy. However, this does not always happen in real life.

There must therefore be a reason in women that determines the sex of the baby (as confirmed by the fifth piece of information). This reason is affected by hot weather and salty food (as confirmed by the second and third pieces of information). It also stands for the hindrance of the fast male sperms from preceding the female ones (first piece of information). What can this reason be?

Is it the acidity and alkalinity of the secretions of the female genital system (fourth piece of information)? NO This is because the secretions of the female genital system are always acidic, while the semen is always alkaline. The acidity of the vaginal secretions may affect the motility of the sperms, but it does not hinder them from reaching the ovum. In addition, the said secretions are not affected by summer or salt.

Is it the ovary? NO

This is because the ovary is the factory for producing the ovums and is governed by hormones. Either it produces ovums or not and it has no relation with determining the baby's sex.

Is it the uterus? NO

This is because the uterus has no relation with fertilization. It is only a place for containing and nourishing the embryo.

Is it the cervix? NO

This is because a normal cervix plays no role in the fertilization process. It only acts as a transport medium to spermatozoa. There are two pathological cases for the cervix; either it has increased viscosity or develops antibodies against the spermatozoa. In the first case, it was scientifically proven that the male sperm can penetrate a viscous environment more rapidly than a female sperm. Accordingly, viscosity is not the reason behind determining the baby's sex. In the second case, antibodies attack both the male and female sperms, causing infertility. They, thus, have no relation with determining the baby's sex. We are only dealing with normal cases not pathological ones.

Is it the fallopian tube? NO

This is because the fallopian tubes act as a carrier for the ovum. They play no role in the fertilization process, just like the uterus.

Is it the ovum ? YES

This is because the ovum is the final and definitive destination in the fertilization process. If the faster and lighter male sperm is able to penetrate the ovum before the female sperm, the offspring will be a boy. Otherwise, the larger and stronger female sperm will be able to continue penetrating the ovum wall and the offspring will be a girl. Hence, the ovum wall is the factor that determines the sperm that will enter the ovum, whether it is the smaller and weaker but faster male sperm or it is the larger and stronger but slower female sperm.

The ovum wall is the factor that determines the baby's sex. There is no other explanation. If the ovum wall of a woman is thin, the small and fast male sperm, carrying a little amount of Hyaluronidase (that can digest &penetrate the ovum wall), can reach the ovum first and easily penetrate its coat. This woman will always give birth to boys.

Figure 1:
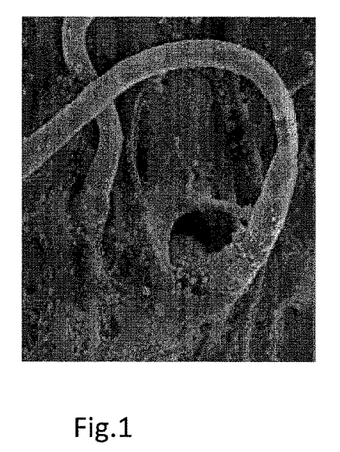
FIG. 1 illustrates a female sperm penetrating the thick coat.

On the other hand, if the ovum wall of a woman is thick, then the male sperm will not be able to digest and dissolve the coat. This is because a male sperm carries a little amount of Hyaluronidase, is light and has less ability of forward progression that helps in penetrating the thick coat. In this case, the larger female sperms, more capable of forward progression and having a larger amount of Hyaluronidase, will be able to penetrate the already weakened thick coat by the vain attempts of the male sperms. Accordingly, the offspring will always be a girl as shown in FIG. 1.

In case the ovum wall is of an average thickness, then if the male sperm can penetrate the coat before the female one, the offspring will be a boy. If the male sperm is not able to penetrate the coat and this mission is accomplished by the female sperm, then the woman will give birth to girls. If the coat tends to be thin, then there is a better chance for giving birth to boys. If the coat tends to be thick, then there is high probability that the offspring will be a girl.

This assumption is derived from real life as there are women who give birth to an equal number of males and females, while others may give birth to one boy and several girls or vice versa.

The phrase "comes on top" in this Hadith: "If man's fluid comes on top, then the child will resemble the father, and if the woman's fluid comes on top, then the child will resemble the mother," has diverse meanings in Arabic. Its intended meaning shall be related to modem science and the above-derived information. The following are some of its meanings:

1. To outstrip something or someone. Allah (Glorified be He) says: " . . . and in no way will We ever be outstripped." (Surat Al-Ma'arij, verse 41). In the Hadith narrated by Thawban (may Allah be pleased with him), the Prophet (peace be upon him) said, "If man's fluid comes on top of a woman's, then the child will be a boy if Allah so wills, and if a woman's fluid comes on top of a man's, then the child will be a girl if Allah so wills." (Related by Imam Muslim)

Imam Abu Bakr Ibn Al-Arabi, Imam Al-Qurtubi in his Tafsir, Imam Ibn Hajar Al-Asqalani in Fath Al-Bari fi Sharh Sahih Al-Bukhari, and Ibn Al-Qayyim in At-Tibyan says that the phrase "comes on top" in the Hadith means "to precede". This means that if a man's fluid (i.e. male sperm) precedes a woman's (i.e. female sperm), the child will be a boy if Allah so wills and vice versa.

2. To come after something or someone. It means that man's sperm comes after the woman's sperm and vice versa. In other words, this means that intercourse should take place before the ovum is released from the ovary so that male and female sperms would spread through the uterus and the fallopian tubes within a period of 20-120 minutes. When the ovum ruptures from the ovary, it is taken by the fimbriae of the fallopian tubes to admit it into the ampulla where it resides on top of the sperms already swimming inside the tube waiting for the ovum to fertilize it. This is how a woman's fluid comes after (or on top of) the man's fluid. On the other hand, when man's fluid comes on top of the woman's, this means that the ovum is released first and the sperms come after.

For example, when we say that the flood comes on top of the valley, we mean that it inundated the trees and rocks at the bottom of the valley. The trees and rocks are already in the valley and the flood comes after them.

How can we utilize this meaning in our present invention?
(a) Boy-desiring couples shall have intercourse after being sure that the ovum is already released from the ovary so that the male sperm (Y) can reach it first. If the ovum wall is thin, the baby will be a boy if Allah so wills. If the ovum wall is thick, the male sperm will not be able to penetrate the ovum and its vain attempts will continue until the female sperm would come and penetrate the ovum. In this latter case, the baby will be a girl if Allah so wills. If the coat is of an average thickness, then there is a better chance for having a baby boy, since male sperms are faster and have enough time to penetrate the ovum before the arrival of the female sperms.
(b) When intercourse takes place before the release of the ovum, then both male and female sperms will already be in the fallopian tubes waiting for the ovum. When the ovum is released and if its coat is thin, then there is a 30% chance of having a baby boy and a 70% chance of having a baby girl. This is the same percentage (i.e. 1:2.8) of size and strength between the male sperm and the female one. If the ovum wall is thick, then there is a 99% chance of having a baby girl. If the ovum wall is of an average thickness, then the percentage of having a girl is about 85%. This is why most infants are girls recently.
(c) If intercourse takes place two or three days before ovulation, then the smaller and weaker male sperms will die, leaving space for the larger and stronger female sperms, which can live up to seven days, to fertilize the ovum once released from the ovary.

3. Both the above-mentioned meanings have one outcome; determining the environment in which the sperms swim and the environment in which the embryo grows. This deduces that the environment in which the embryo grows helps in expressing their genetic traits, which stand for their resemblance. It is known that the vaginal secretions are acidic while the seminal fluid is alkaline. If acidity is more than alkalinity, whether in terms of quantity or concentration, then the female sperm will be more active than the male one and the environment in which the embryo grows will be acidic. Accordingly, the genetic traits passing to the embryo will be those of the mother and the embryo will then resemble her (this is inclusive of blood acidity as well). If alkalinity is more than acidity (whether in volume or concentration of the seminal fluid), then the male sperm will be more active and the environment in which the embryo grows will be alkaline. Accordingly, the genetic traits passing to the embryo will be those of the father and the embryo's resemblance will be to the father (inclusive of the mother's blood alkalinity as well).

The terms "man's fluid" and "woman's fluid" are broad. They may refer to the sperm, i.e. male sperm (man's fluid) and female sperm (woman's fluid). Allah says: "And that He created the two pairs, the male and the female. From a sperm drop when it is ejaculated." (Surat An-Najm, verses 45-46) Sperm drop refers to the male sperm and the female one.

Man's fluid and woman's fluid: The terms are used for referring to the alkaline seminal fluid (consisting of sperms and secretions of the seminal vesicles and prostate) and the secretions of the female acidic genital system (consisting of the secretions of the vaginal mucus membrane, uterus, cervix, fallopian tubes, Bartholin's glands, and the newly discovered prostate-like gland in the posterior vaginal fornix.

This indicates the following:
(a) Precedence of sperms
(b) The baby's resemblance (i.e. the environment in which the embryo grows)

It is known for genealogists that controlling the environment in which the embryo grows helps in expressing some of the genetic traits and concealing other ones. This linguistic usage was used for interpreting the Hadith: "If man's fluid comes on top . . . ."

Man's fluid and woman's fluid: The terms are used for referring to sperm and ovum, respectively. This helped in interpreting the Hadith: ". . . comes on top" to be denoting "comes after."

By considering the interpretation of the above-mentioned verses of Surat Ash-Shura, Hadiths and deductions, I came out with the theory of " ovum wall thickness". The theory is based on the fact that the ovum wall is the main factor for determining the baby's sex. One other factor is the timing of intercourse. The main factor affecting the ovum wall is salt.

If the ovum wall is thin, a woman shall give birth to a baby boy if Allah so wills.

If the ovum wall is thick, a woman shall give birth to a baby girl if Allah so wills.

If the ovum wall is of an average thickness, a woman shall give birth to boys and girls.

A woman may not be able to give birth either because of being infertile or because of the husband's infertility.

I started searching to find grounds for my proposed theory. I tried to find answers to questions like: Has the ovum wall ever been measured? What is the composition of the ovum wall?

I browsed the internet and found no studies made to measure the ovum wall. On the other hand, I found comprehensive studies on the composition of the ovum wall. References of anatomy, such as Gray, mentioned that the ovum wall is composed of three elements:

1. Corona radiata
2. Zona pellucida
3. Ovum plasma membrane

Figure 2:
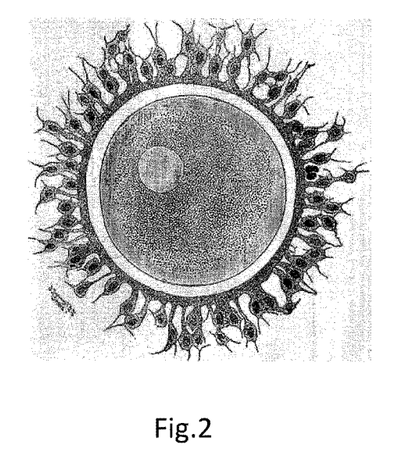
FIG. 2 illustrates corona radiata cells.
Figure 3:
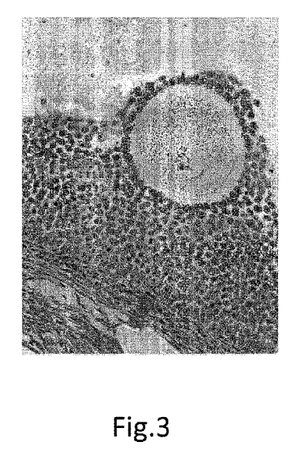

Corona radiata are cells from the ovary that encapsulate the ovum before its breakthrough therefrom (as shown in FIGS. 2 & 3). Scientific references and medical researches mentioned that the ovum wall—especially corona radiata and zona pellucida—differs from one woman to another. For example, the medical site of the School of Medicine, Michigan University (Medical Histology Learning Resources, University of Michigan, Medical School), and the medical site of Wellesly College (dsmith@wellesly.edu-Biology department) said that the corona radiata encapsulating the ovum is made of one layer or more. The famous medical site, Gray Anatomy (Henry Gray. Anatomy of the Human Body), in the section of Embryology, published that the corona radiata encapsulating the ovum is made of 2-3 layers. The medical site of Human Histology, when talking about the ovum, said that the corona radiata encapsulating the ovum is composed of 4-6 layers of cells. The medical site on Histology, Weiss, said that corona radiata encapsulating the ovum is composed of several layers ($5^{th}$ ed., pp. 923-6). The medical site of the School of Medicine, Texas University ((University of Texas, Medical-Branch-cell-biology-graduate-program-ovary . . . preovulatory) published by Linda Spurger) said that the cells encapsulating the ovum are made of 6-10 layers.

I, thus, deduced that all the cited references list reports correct findings. The findings were based on what the researchers saw in an ovum. The saw an ovum only surrounded by one layer of corona radiata, and saw others surrounded by two, three, four, five, six or even more layers (as shown in FIGS. 5-10). Such findings were written down in references. This confirms that the ovum wall differs from one woman to another. Accordingly, it proves that the theory of the thickness of ovum wall is correct. I also deduced that corona radiata secretes the gelatin composing zona pellucida. If corona radiata has an increased number of layers, the zona pellucida will have an increased thickness. If corona radiata has a less number of layers, the zona pellucida will be of a lesser thickness.

The theory of the thickness of the ovum wall, being thus proven correct, I still had to figure out how hot weather and salt attenuate the ovum wall and what is the relation between hot weather and salt.

Finding an answer to the second question, what is the relation between hot weather and salt, was easy. Hot weather increases man's sweat and perspiration tends to concentrate salt in the human body.

But how can salt attenuate the ovum wall? I could not find an answer to that question until one day when I was reciting Surat Al-Anbiya' in the Qur'an, I stopped at the verse " . . . and of water We have made every living thing . . . " (Verse 30) Thinking deeply of this verse, I found that life, soul and water are inseparable. The percentage of water varies among living things and species and even among the different stages of a one living thing. For example, the amount of water in the body of a child is 80:90%. The body of adult men contains 60% of water while that of adult women contains 50%. The percentage of water declines in old age, reaching below 50% in old men and 40% in old women.

Let's compare the bones of living and dead bodies. We will find that the body composition is the same but the amount of water is different. A living human body has much amount of water unlike a dead body. Water confers strength and rigidity to living bones, whereas the bones of a dead body are brittle and can easily be rotten. The Qur'an relates the story of a disbeliever who came to the Prophet (peace be upon him) carrying old bones of a camel and asking: ". . . Who will give life to the bones (after) they are rotten?" (Surat Yasin, verse 78). Allah replied: "Say, "He will give them life, (He) Who brought them into being the first time . . . " (Surat Yasin, verse 79)

Hence, water is a source of life and strength. For example, the skin of a baby is soft whereas that of an old man is coarse. A baby's skin is strong and soft, hard to be wounded, and can quickly be healed. In addition, it can withstand bad weather. On the other hand, an old man's skin is coarse, dry and weak. It can easily be wounded and hard to heal. Water stands for those differences between the two types of skin.

The same applies to lips. Dehydration causes the evaporation of moisture, leaving lips dry and chapped. Applying cocoa butter prevents water evaporation and remoistens the lips. Leaves present another good example of water being a source of life. A green leaf is strong, whereas a fallen one is weak and can easily be broken. This is because the former has more water than latter.

Considering the above-mentioned facts, I came out with the theory of cell fragility. Water is a point of weakness and strength for the ovum wall, which differs among women. Salt takes water out of the cells of the ovum wall, leaving it fragile and weak. When a woman's salt intake decreases, the percentage of water in the cells of the ovum wall increases and the ovum wall becomes thus strong and thick. For example, the cells of a diarrheic child are dehydrated due to loss of body fluids, causing skin loss of elasticity. A decrease in skin turgor is indicated when the skin is pulled up by the thumb and forefinger for a few seconds and does not return to its original state. Loss of skin turgor is a sign of dehydration. Sunken eyes present another sign of dehydration.

Other observations are the following:

1. The percentage of boys born in poor neighborhoods is greater than those born in rich neighborhoods.
2. The percentage of boys born in developing countries is greater than those born in developed ones.
3. Women used to eat salty foods, such as pickles, mesh cheese and salted fish, have a better chance to give birth to boys than those used to eat sweets and sugary foods.
4. Women giving birth to boys tend to have high or normal blood pressure whereas those giving birth to girls tend to have low or normal blood pressure.

5. The percentage of giving birth to females has increased due to obstetricians' recommendation for couples to have daily intercourse starting from day 11 until day 16 after the start of the menstrual cycle.
6. Sugar was first discovered 200 years ago and was consumed only by kings and the rich. Afterwards, it spread among common people, causing the spread of diabetes. Diabetes, insulin and sugar thicken the ovum wall and lead to the birth of females.
7. Obstetricians prescribe Clomid (or Clomifene citrate) to stimulate ovulation. It increases the secretion of FSH, which in turn increases the number of layers of corona radiata encapsulating the ovum.
8. Beautiful women tend to give birth to females than less beautiful ones.
9. There is a better chance for women tending to give birth to females to give birth to males when getting old. This is because the fertility hormones, especially FSH, decrease thus, causing a decrease in the thickness and strength of the ovum wall. This was circulated by old women's folktales and also confirmed by a medical study published online. It was scientifically proven that the two hormones, estrogen and testosterone, retain salt in the body. A scientific study proved that women who secrete much estrogen and testosterone tend to give birth to males.
10. In the past, women used to urinate and defecate outdoors. Afterwards, they used squat toilets and were used to wash their clothes in washtubs. This helped them in delivering their babies by vaginal birth. Upper classes using western toilets, on the other hand, suffered from stiffen pelvis. Accordingly, they used to undergo cesarean section to deliver their babies. Their chances of being able to give birth even decreased. Not having to do much work and being able to afford dessert-rich diet caused upper class women to give birth to females.

In order to prove the correctness of my theory, I started searching in physiology. I focused on osmotic pressure, which deals with studying dissolved salts in the body and their relation with water, especially NaCl. I searched in many modern medical references, including Kumar 2002 and Krant 2003 (CMDT), two of the most known and accredited medical references in the world. Unexpectedly, medical references cited that salt is totally responsible for the entry and exit of water to and from all the body cells.

Before citing those scientific facts, I shall first give the following scientific introduction to ease understanding:
The body of an adult man contains 60% of water.
If the weight of an adult person is 70 kg, then his body shall contain 42 liters of water distributed as follows:
28 liters inside the cells (i.e. intracellular region) (40%)
9.4 liters among the cells (i.e. intercellular region) (13.4%)
4.6 liters inside blood vessels (i.e. plasma) (6.6%)
Osmotic pressure controls the distribution of water in the above-mentioned three sections.

What is osmotic pressure? It is the ability of molecules to attract water (it is also called molecules adhesion strength). Bring a basin and use a foil to divide it into two halves then fill one half with water. Water will easily pass to the other half of the basin and both halves will thus have an equal amount of water. Put 1 kg of sugar, consisting of glucose molecules, into one half of the basin. The glucose molecules will draw a certain amount of water equal to the number of glucose molecules. Replace sugar with 1 kg of salt in the same half of the basin. Salt molecules, being made of sodium and chloride, will draw twice the amount of water drawn by glucose. Hence, the osmotic pressure of salt is twice than that of sugar.

Where is salt in the human body? What is the benefit of a strong osmotic pressure? A human body consists of three sections in which water flow according to the osmotic pressure of each section. The first intracellular section is separated from the second intercellular section by the cell coat (foil in the experiment) and the second intercellular section is separated from the blood vessels by the coat of the blood vessels (foil as well):
1. Water and glucose can easily pass through the three sections in the absence of other molecules.
2. Each section has its own molecules, which control the strength of the osmotic pressure (i.e. the ability to attract water thereto). Those molecules are as follows:
(a) Potassium salts within the cells (intracellular region) (Magnesium salts are ineffective within the cells)
(b) Sodium salts outside the cells (intercellular region), especially sodium chloride
(c) Human proteins inside blood vessels (plasma), especially albumin The main characteristic of the three molecules is that each one of them cannot leave its assigned section.

For example, human proteins cannot pass through the coat of the blood vessels to the intercellular region. Sodium salts cannot pass through the coat of a living cell from the intercellular region to the intracellular region. Potassium salts cannot pass through the coat of a living cell from the intracellular region to the intercellular region because of the existence of a pump in the cell coat that keeps potassium inside the cell at a concentration of 160 millimole and keeps sodium outside the cell at a concentration of 144 millimole. This pump is called Na-k ATPase (Kumar, p. 668).

We can deduce from the above-mentioned observations that sodium salts (and chloride) are the main factor and measurement of the amount of water outside the cells in the intercellular region.

Accordingly, if one's intake of sodium chloride salts increases, salts will precipitate in the intercellular region. This will increase the osmotic pressure of the said region, and will thus draw water from inside the cells, leaving them fragile and weak.

The following experiment was conducted (Kumar, p. 668):

A solution of equal amounts (glucose, saline and albumin, one liter each) was administered intravenously to observe where it will precipitate. The following results were found:
1. Glucose (5% glucose+water): The solution was freely distributed among the three regions.
2. Saline (9% sodium chloride+water): The solution was distributed among the three regions but precipitated in the intercellular region (i.e. outside the cells).
3. Albumin: The solution was not distributed and precipitated inside the blood vessels.

From the above-mentioned results, I came up with irrefutable evidence that sodium chloride (table salt) has the ability to draw water from the layers of corona radiata encapsulating the ovum, causing it to be fragile and weak. The faster male sperm will, thus, be able to penetrate the ovum and the woman will give birth to boys. On the other hand, women depending on low sodium diet have a greater percentage of water inside the cells encapsulating the ovum. The ovum will, thus, be strong, flexible, and hard for the male sperm to penetrate. In this case, the stronger female sperm will be able to fertilize the ovum, causing conception with girls. Other women have an ovum wall of an average thickness. The fourth type of women cannot give birth at all. These are thus the four types mentioned in Surat Ash-Shura.

Sodium chloride may attenuate the ovum wall by two means:
1. Drawing water from inside the cells encapsulating the ovum, causing them to be weak and fragile
2. Increasing the fluid encapsulating the ovum inside the ovary (an intercellular fluid), thus causing a strong rupture of the ovum and removing many layers of corona radiata Increasing the fluid encapsulating the ovum may trigger earlier ovulation. Medical researches demonstrated a close relationship between early ovulation and giving birth to boys. For example, in a 1995 article in Human Reproduction, Weinberg, Baird, and Wilcox suggest that the length of the follicular phase (the time between menstruation and ovulation) is related to the sex of the baby. They suggest that cycles with shorter follicular phase lengths are slightly more likely to result in male babies, while cycles with longer follicular phases are more likely to result in female babies.

It is also worth mentioning that there may be relationship between genetic traits and the number of layers of corona radiata.

A question raises itself for me: Can a drug be used to quickly preserve sodium inside the body and make the ovum wall thinner? It is well known that it requires many years to preserve salt in the woman's body until the ovum wall becomes constantly thinner. I started searching for a drug for preserving sodium chloride in the body of a woman having a thick ovum wall. After searching in pharmacology, herbology and medical references, I found the following three compounds:
1. Aldosterone
2. Fludrocortisone
3. Licourice Aldosterone is a naturally-secreted hormone that absorbs sodium from the kidney channels before being secreted into the urine to be returned to the blood.

Fludrocortisone is a member of the Mineralocoritcoid group. it works exactly as Aldosterone. Skwebb Co., the company manufacturing Fludrocortisone, mentioned in its medical web site and the prescription accompanying Florinef tablet, that skin thinning and fragility are side effects of the drug. Such side effects extend to other cells of the body as well.

The natural Licourice increases the effect of natural cortisol inside the body for preserving a greater amount of the sodium in the body.

It has been also discovered that the following drugs can result in male babies:

Diuretics that discharge big amount of water so that salts are concentrated inside the body, especially sodium that draws water from body cells in turn. I have chosen the Bumetanide diuretic which has less side effects than Frusemide and which helps in potassium and hydrogen ions secretion and leads to reabsorption of sodium and bicarbonate ions.

Sodium bicarbonates (taken orally) increase the alkalinity of both blood and vaginal secretions. If used as a vaginal wash, it turns acidic vaginal secretions into alkaline ones.

Drug Ingredients:

The following is an illustration of the Baby Love Male Capsules, the suggested concentrations of active ingredients thereof, manufacturing method thereof and the best way to use it:

Baby love male capsules consist of the following:
1. Active ingredients:
a) Fludrocortisone (0.1 mg)
b) Bumetanide (0.5 mg)
c) Sodium bicarbonates (9.4 mg)
d) Sodium Chloride (600 mg)
e) Glycyrrhizinate (390 mg)
2. Inactive ingredients Gelatin from which the two-piece hard gelatin capsule is made (000 size). It is extracted from animal bones and skin.
Plasticizers, such as glycerin and sorbitol
Humidity-absorbing agents, such as aluminum oxide
Conservatives, such as sodium citrate.
Sodium chloride is used as a tension neutralization agent, a lubricant and capsule extender. It also acts as a source of sodium and chloride since the body needs 5 to 12 g of them per day. A harmful dose of sodium and chloride reaches 1000 g per day, while a lethal dose reaches 2.5 g/kg per day (for mice).

The following steps increase the chances of having a male child:

Taking baby love male capsules starting from the first day of menstruation One capsule should be taken after eating twice a day continuously until evolution follow-up and ovum release; it usually lasts for 13-17 day of menstruation.

Vaginal washing with bicarbonate sodium (available in pharmacies) A small spoon of bicarbonate sodium should be added to one liter of warm water for washing the vagina until its farthest point 15 minutes before intercourse, a vaginal shower can be used if necessary.

Intercourse is not permitted before ovulation (i.e. the ovum release from the ovary)

I have noticed, during the research process, that ovulation in women with male babies occur early (on day 12 or 13), unlike women with female babies whose ovulation timing occurs later (day 16, 17, 18 or 19). The following research tackles this point:

In a 1995 article in Human Reproduction, Weinberg Baird, and Wilcox suggest that the length of the follicular phase (the time between menstruation and ovulation) is related to the sex of the baby. They suggest that cycles with shorter follicular phase lengths are slightly more likely to result in male babies, while cycles with longer follicular phases are more likely to result in female babies.

I think this relates to the thickness of the graafian follicle wall and the ovary wall. The ovum, as a result, takes a long time to be released. Ovums are released easier and earlier in women with thin ovary wall (ovulation days start from day 10 to 19 of menstruation). It has been scientifically proven that the ovum can be released during one of the three feminine hormonal waves: from day 10 to day 12, from day 13 to day 15, from day 16 to day 19 of menstruation respectively.

Is it possible that both ovaries differ in thickness?

It is well-known that women have a right and left ovary, each releases one ovum per month in turn. If one of them has a thinner wall and hence releases a thin ovum, the woman may get pregnant with a male child. If the other has a thicker wall and hence releases a thick ovum, the woman may get pregnant with a female child. Actually, some women give birth to a male baby in their first pregnancy and give birth to female babies in their second pregnancy and so on. The different thickness of both ovary walls is likened to the difference in both testes in 60% of men, where the left one is bigger and more drooping. However, more research is needed for this piece of information to be accredited.

Can one sperm fertilize the ovum?

Figure 4:
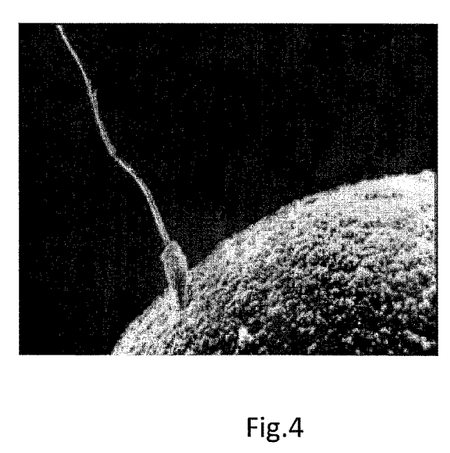
FIG. 4 shows the ovum surrounded by corona radiata.
Figure 5:
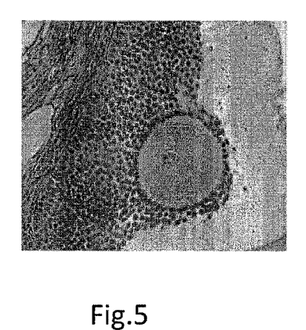
FIG. 5 shows the ovum surrounded by corona radiata.
Figure 6:
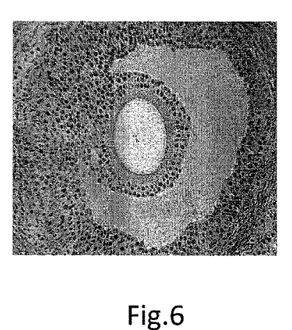
FIG. 6 shows the ovum surrounded by corona radiata.
Figure 7:
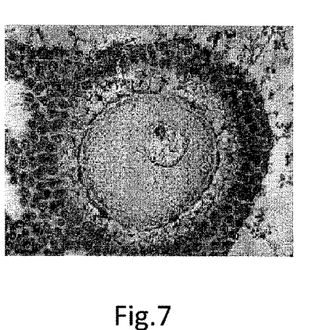
FIG. 7 shows the ovum surrounded by corona radiata.
Figure 8:
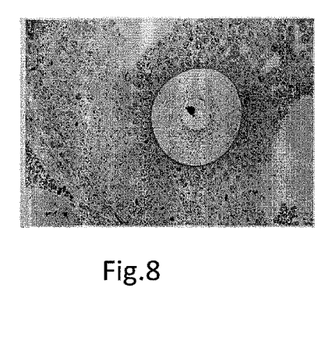
FIG. 8 shows the ovum surrounded by corona radiata.
Figure 9:
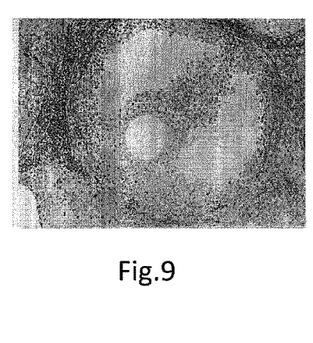
FIG. 9 shows the ovum surrounded by corona radiata.
Figure 10:
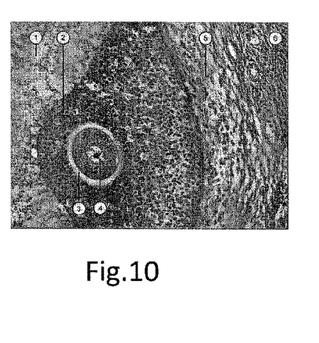
FIG. 10 shows the ovum surrounded by corona radiata.

Yes it can, if the ovum wall is thin and the sperm still retains its strength after its long journey for reaching the ovum, as illustrated in FIG. 4.

Women are advised to do the following:

Eating a lot of salty foods (the normal human being needs 5-12 g of salt per day Eating all types of vegetables Avoiding fruits, especially citrus fruits such as orange, tangerine, lemon, Seville orange, as well as cabbage, cauliflower and red beet Avoiding sugary foods, juice and sweets. Honey should be used as a sweetener instead of sugar (it has been scientifically proven that sugar and alcohol reduce the sodium content in the body)

Avoiding any type of soft drinks

The woman body weight has no relation to giving birth to male/female babies. Fat women may give birth to male babies while slim women may give birth to female babies and vice versa. The internal body condition and the sodium ratio in the body, rather than the body weight, affect the baby's sex.

Elder women are more likely to give birth to male babies, due to the few hormones and water quantity in their body, leading to weakness and fragility of the corona radiata surrounding the ovum)

Using Clomid tablets (clomiphene citrate) and FSH injections as ovulation stimulator increases the possibilities of having female babies. On the other hand, using Pregnyl 5000 (HCG) injections for ovum release increases the possibilities of having male babies.

If the woman suffers from high blood pressure, she should visit the doctor to keep it at a normal level and monitor it daily.

Men are advised to do the following:

Having seafood-rich diet, which is full of energy, zinc and phosphor, such as fish, shrimp, caviar and estacoza, as well as Halawa Spread, nuts and sweets to increase the sperms' speed.

It has been proven that having a cup of tea, coffee or Nescafe thirteen minutes before intercourse increases the sperms speed (increasing the sperms speed may result in male babies, as mentioned in one of the above-mentioned studies).

Figure 11:
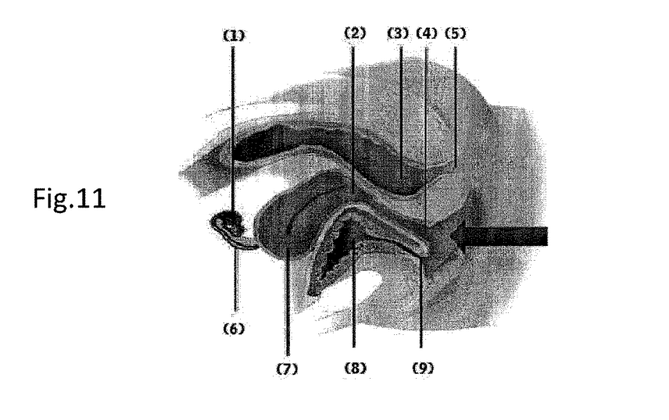
FIG. 11 is a cut-away view of a female pelvis.

The couples should use the dog-like sex position. As illustrated in FIG. 11, the woman should take a prostration-like position for the intercourse to be performed from the back. She should lay afterwards on her back/belly for 2-3 hours. In this way, the uterine would be like a cup filled from above and the sperms would be close to the cervix, making their journey to the ovum more rapidly, thus saving their strength for burrowing the ovum wall.

Avoid smoking; male sperms are generally weaker than female ones, and they become even weaker due to nicotine. Alcohol drinking has the same bad effect.

It has been scientifically proven that the sperms are produced in the testes during 62 days. They should be kept safe during this period by avoiding any thing that may harm them, such as:

1—X rays that may result in sperm and embryo deformities and that weakens the testes production after a while, as happens with workers using X ray machines.

2—Insecticides and chemicals (they have the same side effects of X ray)

3—High body temperature, especially high testes temperature due to:

a—Hot-water shower b—Duties that require long standing under high temperature, such as baking, cooking, working in iron and steel factories and mines.

c—Testicle varicocele (actually, patients with testicle varicocele may have male babies then female babies and become finally sterile due to the effect of high temperature on the weaker male sperms then the stronger female ones.)

The invention claimed is:

1. Capsules for helping to give birth to males comprising:
(a) 0.1 mg Fludrocortisone;
(b) 0.5 mg Bumetanide;
(c) 9.4 mg Sodium Bicarbonate;
(d) 600 mg Sodium Chloride;
(e) 390 mg Glycyrrhizinate;
(f) gelatin extracted from animal bones and skin;
(g) plasticizers, glycerin and sorbitol;
(h) humidity-absorbing agent, aluminum oxide; and
(i) conservatives, sodium citrate.

* * * * *